US00PP13088P2

(12) United States Plant Patent
Glancy

(10) Patent No.: US PP13,088 P2
(45) Date of Patent: Oct. 15, 2002

(54) PHALAENOPSIS PLANT NAMED '(BROTHER SOPHIA) PINE RIDGE #1'

(75) Inventor: Terry A. Glancy, Homestead, FL (US)

(73) Assignee: Twyford International Inc., Santa Paula, CA (US)

( * ) Notice: Subject to any disclaimer, the term of this patent is extended or adjusted under 35 U.S.C. 154(b) by 0 days.

(21) Appl. No.: 09/895,639

(22) Filed: Jun. 30, 2001

(51) Int. Cl.[7] ..... A01H 5/00
(52) U.S. Cl. ..... Plt./311
(58) Field of Search ..... Plt./311

*Primary Examiner*—Bruce R. Campell
*Assistant Examiner*—Susan B. McCormick
(74) *Attorney, Agent, or Firm*—C. A. Whealy

(57) ABSTRACT

A new and distinct Phalaenopsis Orchid plant named (Brother Sophia) 'Pine Ridgte #1' which produces flowers which are almost entirely covered with purple-violet spots over a white background. The flowers are carried on sturdy, upright, frequently branched racemes. The flowers are long lasting and of thick substance. The foliage is attractively marked with silver blotches and spots. Plants of the new cultivar grow quickly to marketable size. The above features combined make the new cultivar particularly well-suited to commercial production and marketing practices.

3 Drawing Sheets

BACKGROUND OF THE INVENTION

The present invention comprises a new and distinct cultivar of Phalaenopsis Orchid, and hereinafter referred to by the cultivar name, (Brother Sophia) 'Pine Ridge #1'. The new cultivar may be marketed under the name Sea Jewel.

Phalaenopsis comprises a genus of about 55 species of herbaceous perennials; many of which, or the hybrids thereof, are suitable for cultivation in the home or greenhouse. Phalaenopsis are predominantly epiphytic or rock-dwelling, and are native to tropical Asia, the Malay Archipelago, and Oceania. The species typically have 2-ranked fleshy oblong or elliptic leaves affixed to a short central stem (monopodial growth), which vary in size from 5 to 8 inches to over 2 feet. The leaves may be entirely green or mottled with silver grey.

Phalaenopsis orchids, referred to as 'Moth Orchids' in the horticultural trade, are used as cut flowers for the florist trade, or sold as flowering potted plants for the home or interiorscape.

Phalaenopsis produce upright or pendent lateral flowering racemes, often with many showy flowers which open in succession beginning with the lowermost. The flowers possess three sepals, and three petals, the lateral ones are similar. The lowermost petal, called the labellum, is three-lobed and is often more brightly colored than the other flower segments. Flower colors include various shades of pink, white, yellow, and red-brown.

Phalaenopsis Orchids are typically propagated from seeds. Asexual propagation of Phalaenopsis is often done from off-shoots which frequently arise from the lower bracts of the inflorescence. The resulting plants are detached from the mother plant and planted in a suitable substrate. Phalaenopsis Orchids may also be asexually reproduced by tissue culture.

The new cultivar was discovered by the Inventor within the progeny of a cross of the parent plants listed below that was made in 1995. The new cultivar was selected by the Inventor as a flowering plant in a controlled environment in Homestead, Fla. in February, 1997.

Since September, 1997, asexual propagation by tissue culture in a laboratory in Sebring, Fla. has been used to increase the number of plants for evaluation and has demonstrated that the unique combination of characteristics as herein disclosed for the new cultivar are firmly fixed and are retained through successive generations of asexual reproduction.

SUMMARY OF THE INVENTION

The following traits have been repeatedly observed and are determined to be basic characteristics of new cultivar which in combination distinguish this Phalaenopsis as a new and distinct cultivar:

1. Flowers of the new cultivar are densely marked with purple-violet spots over a white background. The labellum is dark red in color.
2. Inflorescences of the new cultivar are tall, frequently branched, and sturdy with long lasting flowers with good substance.
3. Leaves of the new cultivar are elliptic in shape and attractively marked with silver blotches and spots.
4. Plants of new cultivar grow quickly, uniformly, and vigorously.
5. Plants of the new cultivar flower early, producing marketable flowering plants in about 11 months.

Plants of the new cultivar have not been observed under all possible environmental conditions. The phenotype may vary significantly with variations in environment such as temperature, light intensity, and daylength, without however, any change in genotype.

Plants of the new cultivar differ primarily from plants of the parent cultivars in flower color. Perhaps the closest commercial comparison to the new cultivar can be made to seedling-derived Phalaenopsis Orchids which are heterogeneous genetically, and typically lack uniformity in growth vigor, plant growth habit, and flower quality. Since this reference point has inconsistent characteristics, a direct comparison for (Brother Sophia) 'Pine Ridge #1' is not available. The new cultivar is a single genotype asexually-propagated via tissue culture; thus its combined horticultural characteristics listed above are uniform and predictable.

BRIEF DESCRIPTION OF THE PHOTOGRAPHS

Colors in the photographs may appear different from the color values that appear in the detailed botanical description which more accurately describe the new cultivar.

The photograph on the first sheet comprises a side perspective view of a typical flowering plant of the new cultivar grown in a 15-cm container.

The photograph on the second sheet comprises a close-up view of a typical inflorescence of the new cultivar. The plant depicted in these photographs is the original seedling selection grown for about three years under appropriate growing conditions.

The photograph on the third sheet comprises a side perspective view of typical flowering plants of the new cultivar that were about 10 months old and flowering for the first time.

DETAILED BOTANICAL DESCRIPTION

All color references are measured against The Royal Horticultural Society Colour Chart, (1995 edition). Colors and numerical measurements are approximate as plant growth and development depends on environmental conditions and cultural practices such as light level, temperature, water status and fertilization rate, among others, without, however any variance in genotype.

Plants used for the description were 1 to 3 years old and grown in 15-cm containers in Homestead, Fla., in a polyethylene-covered greenhouse with day temperatures about 78 to 96° F., night temperatures about 60 to 82° F., and light levels below 1,000 foot-candles. Information for this description was taken during the winter, 2001.

Botanical classification: Phalaenopsis (Brother Sophia) cultivar Pine Ridge #1.

Parentage: Seedling selected from a cross of the following:

*Seed parent.*—Phalaenopsis cultivar Super Stupid.

*Pollen parent.*—Phalaenopsis cultivar Brother Mirage. The cross listed above has since been recorded by The Royal Horticultural Society under the name Brother Sophia.

Propagation:

*Type.*—Asexual propagation by tissue culture.

*Time to initiate and elongate roots.*—Summer: About 28 days at 82 to 96° F. Winter: About 42 days at 60 to 78° F.

*Time to produce a fully rooted young plant.*—Summer: About 120 days at 82 to 96° F. Winter: About 180 days at 60 to 78° F.

*Root description.*—Very thick, fleshy, and greenish white in color.

Plant description: Under appropriate growing conditions, plants of the new cultivar attain a mature size of about 8 to 10 cm in height (top of leaf plane) and about 34 to 40 cm in width.

Leaf description:

*Form.*—Leaves are elliptic with obtuse apex and cuneate base; margins, entire. The leaf blade is flat or slightly folded upward from the midrib. The upper leaf surface is slightly glossy; young leaves are glossier than fully expanded leaves; the lower leaf surface is dull. Leaves are leathery, thick and glabrous.

*Size.*—Leaf blades of a mature-sized plant are about 18 to 24 cm in length and about 8 to 9.5 cm in width.

*Veins.*—Veins are sunken within the lamina.

*Color.*—Adaxial surface: 137A, with silver-green, 191A, blotches and spots. Abaxial surface: 147B tinged with 187A. Juvenile plants have considerable more purple on the undersides of the leaves that do large mature plants.

Flower/inflorescence description:

*Description.*—The sepals and petals are white in base color, and are nearly covered with purple-violet spots. The sepals are elliptic to ovate in shape, the lateral petals are broadly ovate with a rounded apex. The sepals and petals are flat or slightly cupped. The labellum is deeply three-lobed with two prominent callosities at the central junction of the lateral lobes and base of the midlobe. The lateral lobes of the labellum fold upward about the column, the midlobe extends forward and is teminated by two twisted appendages at the apex. The lateral lobes of the labellum are obovate in shape, the midlobe is triangular. The labellum is dark red in color with yellow markings at the junction of the segments. The callosities are yellow with dark red-purple spots and stripes. The margins of the labellum are tinged with yellow.

*Dimensions.*—Flower: About 7.5 to 8 cm wide, and about 6.5 to 7.5 cm in height. Sepals: About 3.6 to 4.1 cm long, and about 2.6 to 3 cm wide. Petals: About 3.5 to 3.8 cm long, and about 3.5 to 3.7 cm wide. Labellum: About 2.3 cm long, and about 2 cm wide (not flattened).

*Coloration.*—Sepals: Adaxial surface: Base color, white, 155D, nearly covered with purple violet dots which are darker than, but closest to 80A. Abaxial surface: White, 155D, tinged with 80C. Dots of 80A on the adaxial surface are visible thought the sepal on the abaxial surface. Lateral Petals: Adaxial surface: Base color, white 155D, nearly covered with purple violet dots which are darker than, but closest to 80A. Abaxial surface: Base color, white, 155D, tinged with 80C. Dots of 80A on the adaxial surface are visible thought the petal on the abaxial surface. Labellum: Adaxial surface: Red-purple, 59A; with yellow, 13C, markings and speckles and stripes of 59A to 59B at the junction of the segments. Callosities: Yellow 13B to 13C, with fine speckles and stripes of 59A. Abaxial surface: Lateral lobes: White, 155D, with 59A to 59C margins. Midlobe: 82A, with 59A to 59B margins.

*Raceme.*—Dimension: The raceme is about 63 cm from base to tip, and about 0.5 cm in diameter at its midpoint. About 5 to 7 flowers are produced on each raceme. One or two branch spikes, containing 3 to 5 flowers/buds are typically produced. The raceme is 200C and tinged with 147B in color.

*Quantity of flowers and time to flower.*—For an untreated plant as depicted in the photograph on the first sheet which is flowering for the 4th time, about 20 flowers and unopened buds are present. Flowering starts about 3 to 6 months after planting 12-week old liners; first time flowering plants produce about 3 to 4 flowers per raceme.

*Flower longevity.*—Individual flowers maintain good substance and coloration for about two months on the plant. Inflorescences are in flower for about 3 to 5 months on the plant.

*Natural flowering season.*—Plants of the new cultivar typically flower during the winter and early spring in Southern Florida.

Reproductive organs: The stamens, style and stigmas are fused into a single short structure called the column, possessing one terminal anther with pollen grains united into a pollinia, which are covered by an anther cap. The stigma is located under the column behind the pollinia. Ovary inferior, three carpels present.

*Column.*—The column is about 1.2 cm long, about 6 mm wide, and 155D tinged with 82D in color.

*Pollinia.*—Two oval masses of pollen present, about 1 mm in diameter, and 21B in color.

*Stigma.*—Concave, sticky rectangular area, under column, about 4 mm by 3 mm in size, and 155D in color.

*Ovary.*—About 1.1 cm long, about 3 mm diameter, and lighter than, but closest to 82D in color.

*Pedicel.*—About 2.4 cm long, about 4 mm in diameter, and lighter than, but closest to 82D in color.

*Seed.*—Seed production has not been observed.

Temperature tolerance: Plants of the new cultivar have been observed to tolerate temperatures from 45 to 105° F.

Disease/pest resistance: Plants of the new cultivar have not been observed to be resistant to pathogens or pests common to Phalaenopsis Orchids.

General observations: Plants of (Brother Sophia) 'Pine Ridge #1' produce flowers which are almost entirely covered with purple-violet spots over a white background. The flowers are carried on tall, sturdy, upright, and frequently branched racemes. The flowers are long lasting and of thick substance. The foliage is attractively marked with silver blotches and spots. The plant grows very quickly to marketable size.

It is claimed:

1. A new and distinct cultivar of Phalaenopsis Orchid plant named (Brother Sophia) 'Pine Ridge #1', as illustrated and described.

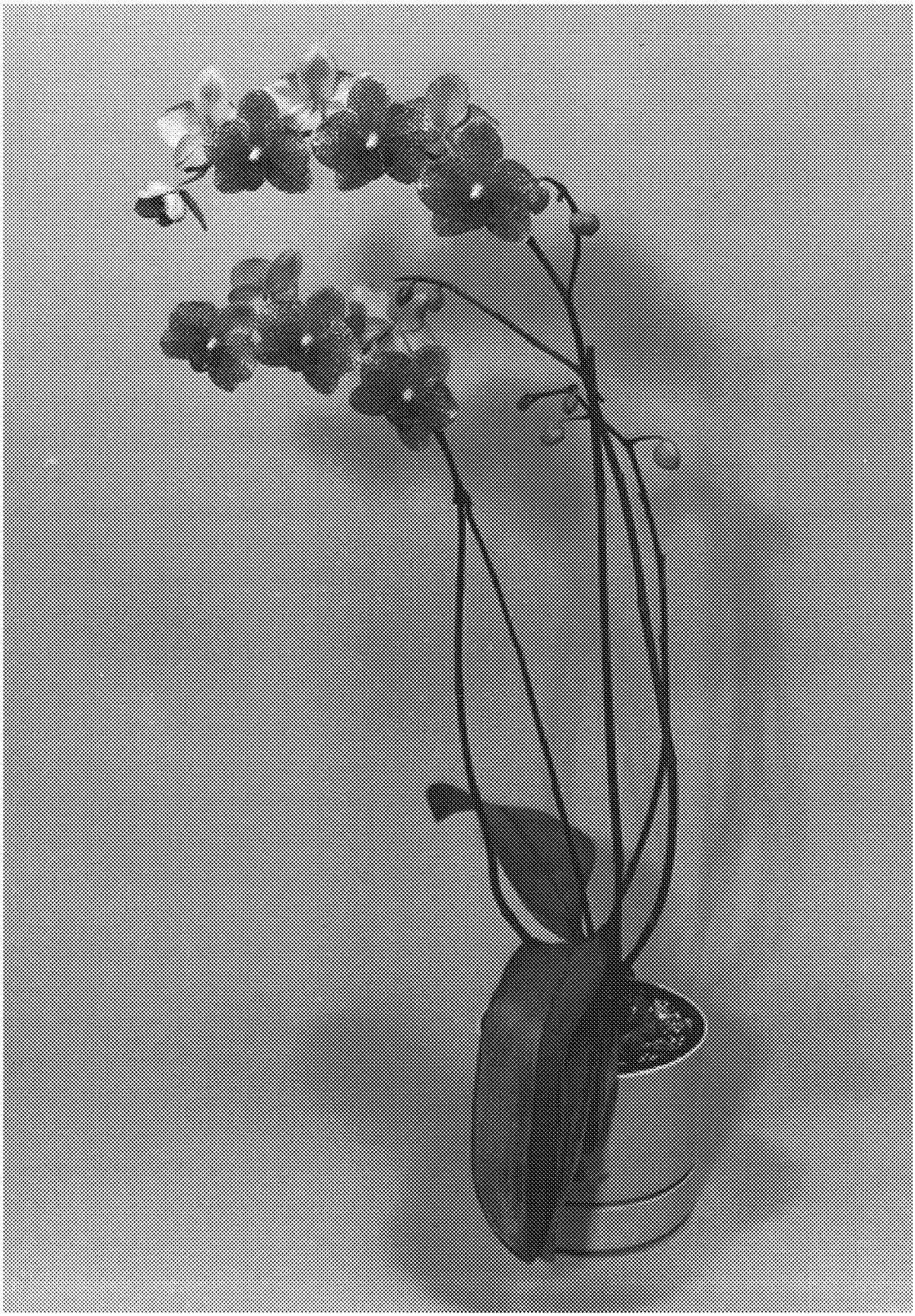

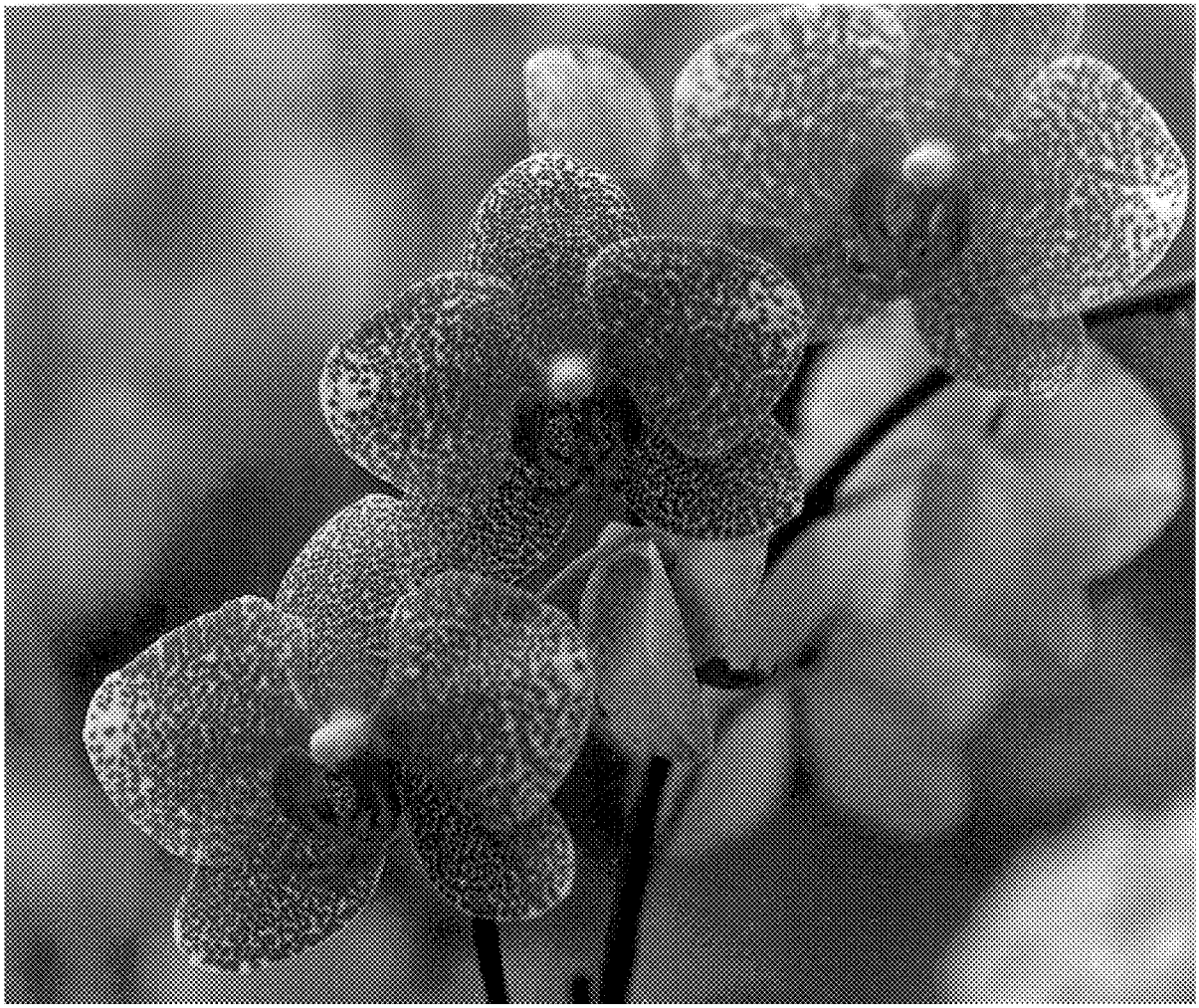

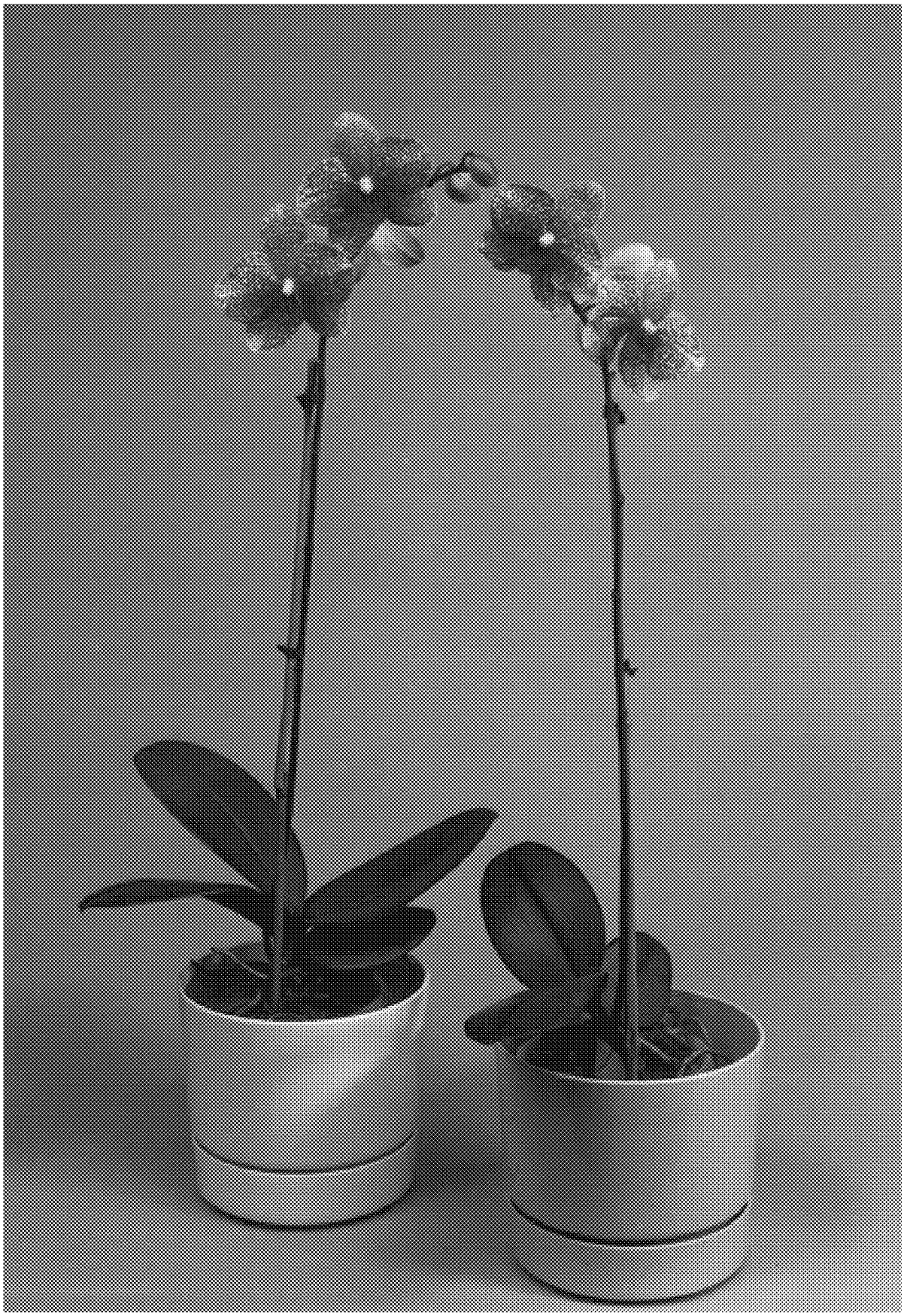

* * * * *